United States Patent
Shiba et al.

(10) Patent No.: US 11,992,265 B2
(45) Date of Patent: May 28, 2024

(54) OPHTHALMOLOGIC INFORMATION ANALYSIS APPARATUS AND OPHTHALMOLOGIC INFORMATION ANALYSIS PROGRAM

(71) Applicant: NIDEK CO., LTD., Aichi (JP)

(72) Inventors: Ryosuke Shiba, Aichi (JP); Tetsuya Kano, Aichi (JP); Yukihiro Higuchi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 432 days.

(21) Appl. No.: 17/366,809

(22) Filed: Jul. 2, 2021

(65) Prior Publication Data
US 2022/0000361 A1   Jan. 6, 2022

(30) Foreign Application Priority Data
Jul. 3, 2020   (JP) .................. 2020-115836

(51) Int. Cl.
*A61B 3/10* (2006.01)
*A61B 3/00* (2006.01)
*G06T 7/00* (2017.01)

(52) U.S. Cl.
CPC ............ *A61B 3/102* (2013.01); *A61B 3/0058* (2013.01); *G06T 7/0012* (2013.01); *G06T 2207/10101* (2013.01); *G06T 2207/30041* (2013.01)

(58) Field of Classification Search
CPC ..... A61B 3/102; A61B 3/0058; G06T 7/0012; G06T 2207/10101; G06T 2207/30041
See application file for complete search history.

(56) References Cited

U.S. PATENT DOCUMENTS

| | | | |
|---|---|---|---|
| 2010/0238403 A1* | 9/2010 | Kobayashi | A61B 3/0025 351/206 |
| 2012/0184845 A1 | 7/2012 | Ishikawa et al. | |
| 2014/0112562 A1 | 4/2014 | Yamakawa et al. | |

(Continued)

FOREIGN PATENT DOCUMENTS

| | | |
|---|---|---|
| JP | 2010-246904 A | 11/2010 |
| JP | 2013-27442 A | 2/2013 |

(Continued)

OTHER PUBLICATIONS

Office Action dated Nov. 28, 2023, issued by Japanese Patent Office in Japanese Patent Application No. 2020-115836.

*Primary Examiner* — John J Lee
(74) *Attorney, Agent, or Firm* — Sughrue Mion, PLLC

(57) ABSTRACT

There are provided an ophthalmologic information analysis apparatus and an ophthalmologic information analysis program capable of efficiently performing follow-up observation of a subject eye. There is provided: a central processing unit configured to: acquire first analysis data obtained by analyzing an analysis region of the subject eye in first OCT data including the analysis region; acquire second OCT data captured on a day different from that of the first OCT data; perform an analysis comprising: specifying the analysis region corresponding to the first analysis data from the second OCT data; and acquiring second analysis data obtained by analyzing the analysis region in the second OCT data; and control a display to display the first analysis data and the second analysis data in a comparable manner.

11 Claims, 10 Drawing Sheets

(56) References Cited

U.S. PATENT DOCUMENTS

2018/0064336 A1* 3/2018 Kano ................ A61B 3/102
2019/0313894 A1* 10/2019 Kano ................ A61B 3/0091
2021/0000338 A1* 1/2021 Tsukada ............. G06T 3/60

FOREIGN PATENT DOCUMENTS

JP         2014-83268 A    5/2014
JP         2018-147387 A   9/2018

* cited by examiner

FIG. 6
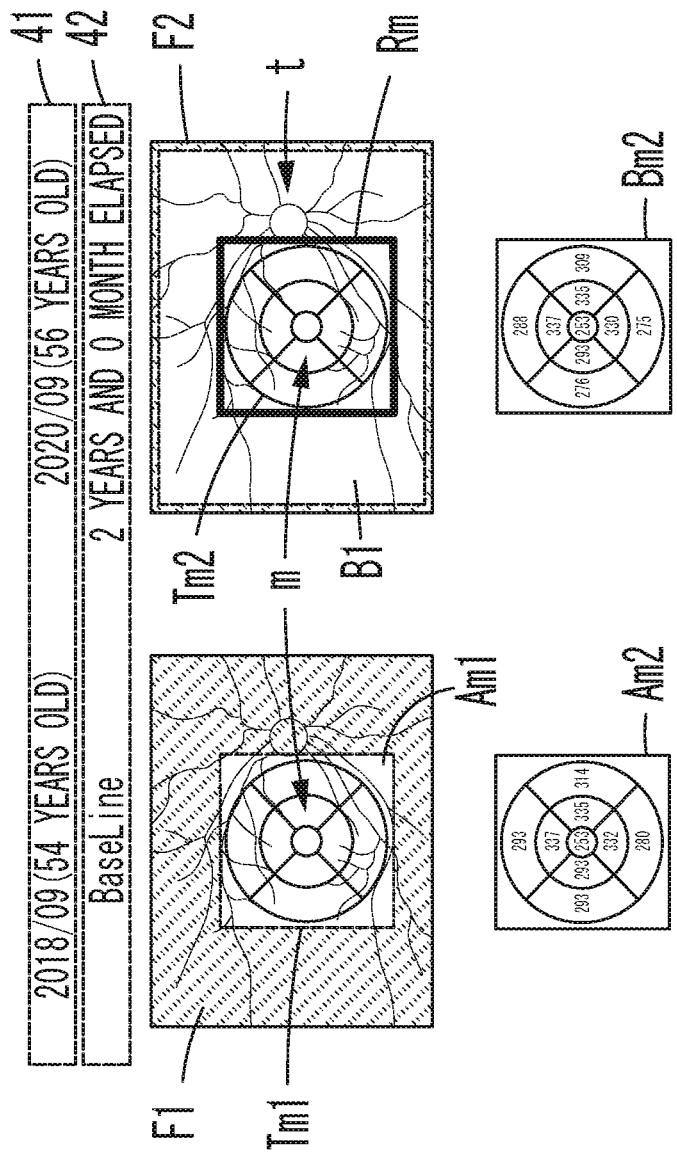
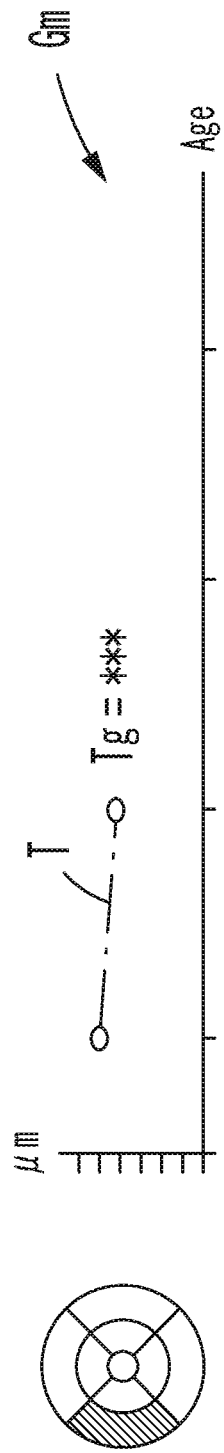

FIG. 7
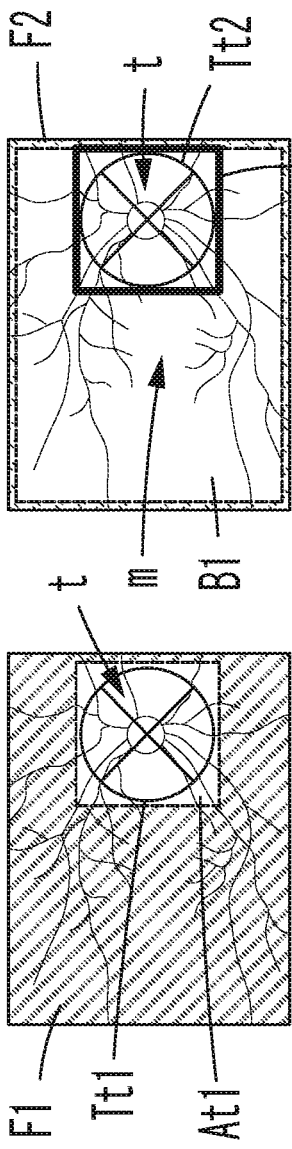
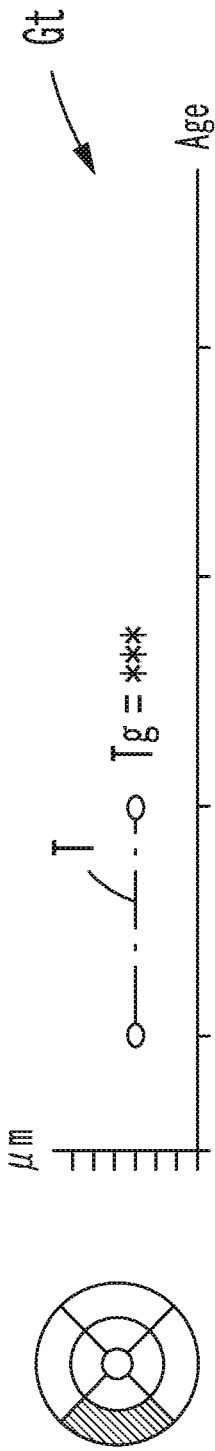

FIG. 10

| | DATA NO. | EXAMINATION DATE | MACULA ▼ | OPTIC PAPILLA ▼ | RETINA MAP ▼ | mm | px |
|---|---|---|---|---|---|---|---|
| ☐ | 1 | 2015/09/20 | × | ○ | × | 6×6 | 256×256 |
| ☒ | 2 | 2015/09/20 | ○ | × | × | 6×6 | 256×256 |
| ☐ | 3 | 2016/09/28 | × | ○ | × | 6×6 | 256×256 |
| ☒ | 4 | 2016/09/28 | ○ | × | × | 6×6 | 256×256 |
| ☐ | 5 | 2017/09/27 | × | × | × | 6×6 | 256×256 |
| ☒ | 6 | 2017/09/27 | ○ | ○ | ○ | 6×6 | 256×256 |
| ☒ | 7 | 2018/09/30 | ○ | ○ | ○ | 12×9 | 512×128 |
| ☒ | 8 | 2019/09/21 | ○ | ○ | ○ | 12×9 | 512×128 |
| ☒ | 9 | 2021/09/16 | ○ | ○ | ○ | 12×9 | 512×128 |
| ... | ... | ... | ... | ... | ... | ... | ... |

OPHTHALMOLOGIC INFORMATION ANALYSIS APPARATUS AND OPHTHALMOLOGIC INFORMATION ANALYSIS PROGRAM

CROSS-REFERENCE TO RELATED APPLICATIONS

This application is based on and claims priority under 35 USC 119 from Japanese Patent Application No. 2020-115836 filed on Jul. 3, 2020, the contents of which are incorporated herein by reference.

TECHNICAL FIELD

The present disclosure relates to an ophthalmologic information analysis apparatus and an ophthalmologic information analysis program for analyzing a subject eye.

BACKGROUND

There is a case where an optical coherence tomography (OCT) for ophthalmology is used to acquire images of the same site of the subject eye on different examination dates and observe the progress. For example, in a case of OCT for fundus, it is possible to acquire a tomographic image of the fundus a plurality of times and observe the progress of a lesion site from the change of the tomographic image (refer to JP-A-2010-246904).

SUMMARY

In the related art, the optical coherence tomography does not assume a difference in the scanning range of the measurement light, and in follow-up imaging for observing the progress of the subject eye, the scanning range set in the first imaging is set to the next and subsequent imaging of the subject eye. In other words, it is necessary to unify the scanning range at the time of imaging.

Recently, the scanning range of the measurement light in the optical coherence tomography has been widened, and it is not possible to compare the imaging result in a narrow scanning range captured in the past with the imaging result in a wide scanning range captured at present.

In view of the above-described related art, a technical object of the present disclosure is to provide an ophthalmologic information analysis apparatus and an ophthalmologic information analysis program capable of efficiently performing follow-up observation of a subject eye regardless of a difference in scanning range.

In order to solve the above-described problems, the present disclosure has the following configuration.

(1) According to a first aspect of the present disclosure, an ophthalmologic information analysis apparatus for analyzing OCT data captured by scanning a subject eye with measurement light by an optical coherence tomography, the apparatus including: a display; and a central processing unit configured to: acquire first analysis data obtained by analyzing an analysis region of the subject eye in first OCT data including the analysis region, the analysis region being obtained by scanning the measurement light in a transverse direction in a first scanning range on the subject eye; acquire second OCT data captured on a day different from that of the first OCT data, the second OCT data including at least the analysis region obtained by scanning the measurement light in the transverse direction in a second scanning range different from the first scanning range on the subject eye; perform an analysis including: specifying the analysis region corresponding to the first analysis data from the second OCT data; and acquiring second analysis data obtained by analyzing the analysis region in the second OCT data, regardless of a difference between the first scanning range and the second scanning range; and control the display to display the first analysis data and the second analysis data in a comparable manner.

(2) According to a second aspect of the present disclosure, a non-transitory computer-readable storage medium storing a program executed by a processor of an ophthalmologic information analysis apparatus for analyzing OCT data captured by scanning a subject eye with measurement light by an optical coherence tomography, the program, when executed by the processor, causing the ophthalmologic information analysis apparatus to perform: acquiring first analysis data obtained by analyzing an analysis region of the subject eye in first OCT data including the analysis region, which is obtained by scanning the measurement light in a transverse direction in a first scanning range on the subject eye; acquiring second OCT data including at least the analysis region, which is obtained by scanning the measurement light in the transverse direction in a second scanning range different from the first scanning range on the subject eye being captured on a day different from that of the first OCT data; an analysis including: specifying the analysis region corresponding to the first analysis data from the second OCT data; and acquiring second analysis data obtained by analyzing the analysis region in the second OCT data, regardless of a difference between the first scanning range and the second scanning range; and controlling a display to display the first analysis data and the second analysis data in a comparable manner.

(3) According to a third aspect of the present disclosure, an ophthalmologic information analysis apparatus for analyzing OCT data captured by scanning a subject eye with measurement light by an optical coherence tomography, the apparatus including: a display; and a central processing unit configured to: acquire first OCT data including an analysis region of the subject eye, which is obtained by scanning the measurement light in a transverse direction in a first scanning range on the subject eye; acquire second OCT data including at least the analysis region, which is obtained by scanning the measurement light in the transverse direction in a second scanning range different from the first scanning range on the subject eye being captured on a day different from that of the first OCT data; perform an analysis specifying the analysis region common to the first OCT data and the second OCT data, regardless of a difference between the first scanning range and the second scanning range; and control the display to display the analysis region common to the first OCT data and the second. OCT data in a comparable manner.

BRIEF DESCRIPTION OF DRAWINGS

FIG. 6 is an example of a display screen related to a macula.

FIG. 7 is an example of the display screen related to an optic papilla.

FIG. 10 is an example of a setting screen.

DETAILED DESCRIPTION

<Overview>

Figure 1:
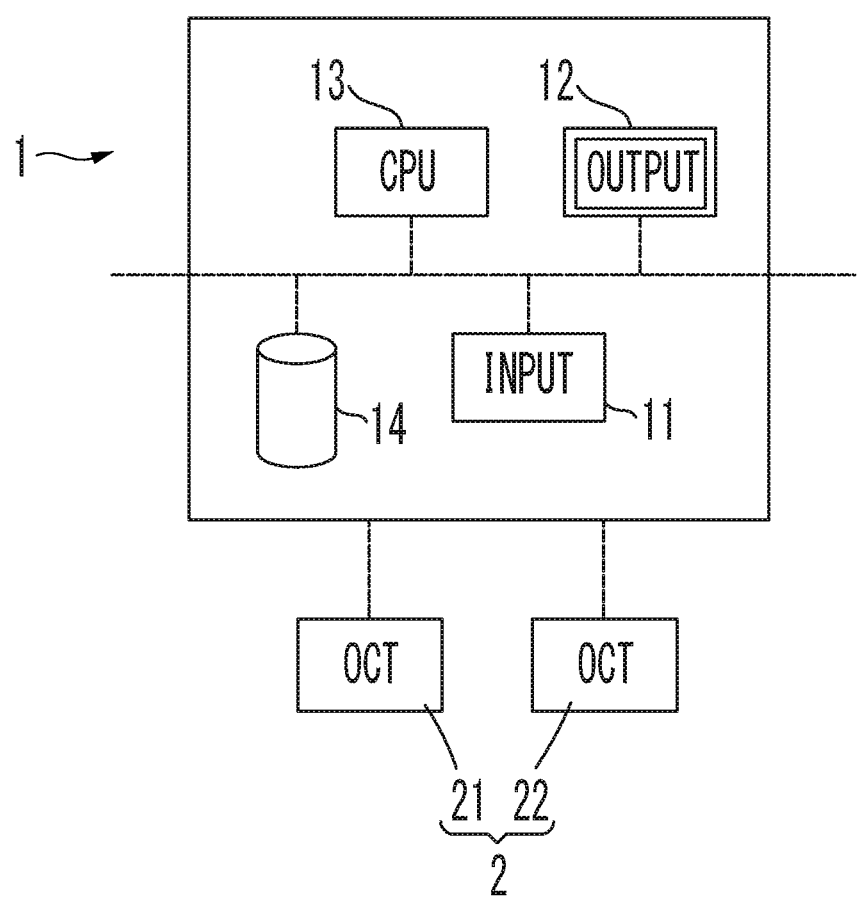
FIG. 1 is a configuration view of an ophthalmologic information analysis apparatus.

An illustrative embodiment of the ophthalmologic information analysis apparatus according to the present disclosure will be described. The items classified by < > below can be used independently or in association with each other.

The ophthalmologic information analysis apparatus of the present illustrative embodiment analyzes OCT data captured by scanning a subject eye with measurement light by an optical coherence tomography (for example, optical coherence tomography 2). For example, the OCT data having different scanning ranges of measurement light, which is acquired at different dates and times by the optical coherence tomography, is analyzed. One example includes the analysis of OCT data having different scanning ranges of measurement light, which is acquired at different dates and times using the same optical coherence tomography. In addition, one example includes the analysis of OCT data having different scanning ranges of measurement light, which is acquired at different dates and times using different optical coherence tomography. The scanning range of the measurement light may be set to ranges different from each other depending on the control of a scanning unit (for example, an optical scanner), or may be set to ranges different from each other depending on the insertion or removal of an optical member.

The OCT data may be signal data or may be image data generated from the signal data. For example, the OCT data may be a tomographic image illustrating the reflection intensity characteristic of the subject eye. In addition, for example, the OCT data may be a motion contrast image of the subject eye. The OCT data may be OCT data in which, in addition to the scanning range of the measurement light, other scanning conditions of the measurement light, detection conditions for detecting the measurement light, and the like are different. For example, the scanning conditions include at least one of a scanning pattern, a scanning position, a scanning site, a scanning angle of view (two-dimensional scanning width in a direction orthogonal to the measurement light), and the like. For example, the detection conditions may be exposure time and the like.

<First Acquisition Unit>

The ophthalmologic information analysis apparatus of the present illustrative embodiment may include a first acquisition unit (for example, CPU 13). The first acquisition unit acquires first analysis data obtained by analyzing the analysis region of the subject eye, example, the analysis region of the subject eye may be any part of the fundus, and examples thereof include macula, optic papilla, and the like.

The first acquisition unit may acquire the first analysis data by receiving the first OCT data captured by the optical coherence tomography and analyzing the first OCT data. The first acquisition unit may acquire the first analysis data by receiving the first analysis data obtained by analyzing the first OCT data, which is captured by the optical coherence tomography, by the optical coherence tomography. The date and time when the first OCT data is acquired and the date and time when the first analysis data is acquired may be the same date and time, or may be different dates and times. For example, such first OCT data may be data obtained by scanning the measurement light on the subject eye in the transverse direction (direction orthogonal to the depth direction of the subject eye) in a first scanning range.

The first OCT data may be a plurality of pieces of OCT data having different first scanning ranges of the measurement light from each other. In other words, the first OCT data may be a plurality of pieces of OCT data having different first scanning ranges from each other in a direction orthogonal to the depth direction of the subject eye. For example, the first OCT data may be a plurality of pieces of OCT data including the first analysis region and the OCT data including the second analysis region different from the first analysis region. In this case, the first acquisition unit may acquire the first analysis data obtained by analyzing the first analysis region and the second analysis region respectively.

In a case where the first OCT data is a tomographic image, the first analysis data may be at least one of information on the thickness of the subject eye, a two-dimensional analysis map image, a two-dimensional analysis chart, analysis values, lesion measurement information, and the like. For example, the information on the thickness of the subject eye may be information on the thickness of at least one layer of each layer of the retina, the choroid, and the like. For example, the two-dimensional analysis map image may be an image generated based on the thickness of the subject eye. Examples include a macula map image, an optic papilla map image, a retina map image, and the like. For example, the two-dimensional analysis chart may be a chart generated based on the thickness of the subject eye. As an example, when the analysis region is the macula, GCHART, S/I chart, ETDRS chart, and the like can be described. As an example, when the analysis region is the optic papilla, an overall chart, a vertical chart, a TSNIT chart, a ClockHour chart, and the like can be described. For example, the analysis value may be a numerical value of the thickness of the subject eye, a C/D ratio of the optic papilla, or the like. The analysis value may be represented by an evaluation value (for example, a 6-step evaluation of A to F, and the like) divided in steps. For example, the lesion measurement information may be at least one of lesion size, area, volume, and the like.

In a case where the first OCT data is a motion contrast image, the first analysis data may be at least one of information on the blood vessel of the subject eye, a two-dimensional analysis map image, and the like. For example, the information on the blood vessel of the subject eye may be information on the blood vessel density, the blood vessel area, the blood vessel volume, the blood vessel diameter, the blood vessel tortuosity degree, and the like. For example, the two-dimensional analysis map image may be a density map image.

<Second Acquisition Unit>

The ophthalmologic information analysis apparatus of the present illustrative embodiment may include a second acquisition unit (for example, CPU 13). The second acquisition unit acquires second OCT data captured at a date and time different from that of the first OCT data, by the optical coherence tomography. For example, the second OCT data may be data obtained by scanning the measurement light on the subject eye in the transverse direction in a second scanning range different from the first scanning range.

The second OCT data may be data including at least the same analysis region as the first OCT data. In other words, the second OCT data may be data including the same analysis region as that of the first OCT data in the direction orthogonal to the depth direction of the subject eye. For example, when the first OCT data is OCT data including the first analysis region, the second OCT data may be data including at least the first analysis region. In addition, for example, when the first OCT data is OCT data including the second analysis region, the second OCT data may be data including at least the second analysis region. It is needless to say that, for example, the second OCT data may be data including both the first analysis region and the second analysis region.

<Third Acquisition Unit>

The ophthalmologic information analysis apparatus of the present illustrative embodiment may include a third acquisition unit (for example, CPU 13). The third acquisition unit acquires third OCT data captured at a date and time different from that of the first OCT data and the second OCT data, by the optical coherence tomography. For example, the third OCT data may be data obtained by scanning the measurement light on the subject eye in the transverse direction in the second scanning range. In other words, the third OCT data may be data captured in the same scanning range as that of the second OCT data.

Therefore, the third OCT data is data including the same analysis region as that of the second OCT data. For example, when the second. OCT data is OCT data including at least the first analysis region, the third OCT data is data including at least the first analysis region. For example, when the second. OCT data is OCT data including at least the second analysis region, the third OCT data is data including at least the second analysis region. For example, when the second OCT data is OCT data including both the first analysis region and the second analysis region, the third OCT data is data including both the first analysis region and the second analysis region.

<Setting Unit>

The ophthalmologic information analysis apparatus of the present illustrative embodiment may include a setting unit (for example, CPU 13). The setting unit sets an analysis region to be analyzed by an analysis unit. For example, the setting unit may set the analysis region to be analyzed by the analysis unit to one or both of the first analysis region and the second analysis region.

For example, the setting unit may set the analysis region based on the operation signal input by an operator operating the operation unit (for example, input unit 11). In this case, the first analysis region and the second analysis region may be set to be switchable, or any one of the first analysis region and the second analysis region may be set to be selectable. For example, the setting unit may automatically set all of the overlapping analysis regions between each of the data as the analysis region.

<Analysis Unit>

The ophthalmologic information analysis apparatus of the present illustrative embodiment may include the analysis unit (for example, CPU 13). The analysis unit specifies an analysis region in the second OCT data corresponding to the first analysis data obtained by analyzing the analysis region of the first OCT data. The analysis unit acquires the second analysis data obtained by analyzing the specified analysis region in the second OCT data.

The analysis unit may specify the analysis region of the second OCT data by using various image processing methods (characteristic point extraction method, method using correlation function, method using Fourier transform, and the like). For example, in this case, by associating the positional relationship between the pixels of the analysis region included in the first OCT data and the pixels of the analysis region included in the second OCT data, the analysis region of the second OCT data may be specified. The analysis unit may specify the analysis region of the second OCT data based on the scanning conditions of the measurement light when the first OCT data and the second OCT data are obtained. For example, in this case, by associating the positional relationship between the first scanning range of the measurement light and the second scanning range of the measurement light, the analysis region in the second. OCT data may be specified.

As the second analysis data, the analysis unit may acquire at least one of the above-described information on the thickness of the subject eye, information on the blood vessels of the subject eye, the two-dimensional analysis map image, the two-dimensional analysis chart, the analysis values, the lesion measurement information, and the like.

The analysis unit can obtain the second analysis data by performing the above-described specification and analysis processing in the second OCT data, regardless of the difference between each of the scanning ranges (that is, first scanning range and second scanning range), which is obtained by imaging the first OCT data and the second OCT data Therefore, even in a case where the scanning range of the measurement light in the optical coherence tomography is widened and the analysis results with different scanning ranges are obtained for the same subject eye, the follow-up observation is efficiently performed.

In a case where the first analysis data obtained by analyzing the first analysis region and the second analysis region included in each of the plurality of pieces of OCT data is acquired by the first acquisition unit, the analysis unit may specify at least one of the first analysis region and the second analysis region corresponding to the first analysis data from the second OCT data. In the second OCT data, the second analysis data obtained by analyzing at least one of the first analysis region and the second analysis region may be acquired. In other words, the second analysis data may be analysis data obtained by analyzing only the first analysis region, or may be analysis data obtained by analyzing only the second analysis region. The second analysis data may be a plurality of pieces of analysis data including the analysis data obtained by analyzing the first analysis region and the analysis data obtained by analyzing the second analysis region.

In a case where the third OCT data obtained by imaging the same second scanning range as that of the second OCT data is obtained by the third acquisition unit, the analysis unit may specify the analysis region corresponding to the first analysis data or the second analysis data from the third OCT data Third analysis data obtained by analyzing the analysis region may be acquired in the third OCT data.

The third OCT data may be obtained as data including the first analysis region. In this case, the analysis unit may specify the first analysis region corresponding to the first analysis data or the second analysis data from the third OCT data. In the third OCT data, the data obtained by analyzing the first analysis region may be acquired as the third analysis data.

The third OCT data may be obtained as data including the first analysis region and the second analysis region. In this case, similar to the description above, the analysis unit may specify the first analysis region from the third OCT data and acquire the third analysis data obtained by analyzing the first analysis region. In this case, the analysis unit may specify the second analysis region corresponding to the second analysis data from the third OCT data, and acquire the data obtained by analyzing the second analysis region in the third OCT data as the third analysis data. It is needless to say that, in this case, the analysis unit may obtain a plurality of pieces of analysis data obtained by analyzing each of the first analysis region and the second analysis region as the third analysis data.

The analysis unit may acquire the analysis data by selectively analyzing the analysis region of the subject eye based on the analysis region set by the setting unit. For example, in a case where the second OCT data and the third OCT data including both the first analysis region and the second analysis region are obtained, the analysis unit selectively analyzes the first analysis region and the second analysis region, and acquires at least one of the second analysis data and the third analysis data for the first analysis region and the second analysis data and the third analysis data for the second analysis region. Accordingly, when the OCT data including the plurality of analysis regions is acquired, the analysis data in the desired analysis region can be acquired, and the change over time can be easily observed.

In the present illustrative embodiment, the analysis unit may be configured to specify a region corresponding to each analysis region by using data different from the OCT data, which is associated with the OCT data of the subject eye. As an example, an OCT front image generated by analyzing the OCT data can be used. In addition, as an example, an infrared front image captured by a fundus camera optical system can be used. Further, as an example, an SLO front image captured by a scanning type confocal camera optical system can be used.

Each OCT data does not necessarily have to be associated with a front image by the same optical system, and at least one of the front image types may be different. As an example, the first OCT data may be associated with the OCT front image, and the second OCT data and the third OCT data may be associated with the infrared front image.

In the present illustrative embodiment, the analysis unit may further acquire the follow-up observation data for observing the progress of the analysis region in the subject eye. For example, by confirming the follow-up observation data, it becomes easier to grasp the tendency of the analysis region with change over time, and the follow-up observation of the subject eye can be efficiently performed.

The follow-up observation data may be statistical information generated from the analysis data, or the like. For example, the statistical information may be numerical values or charts. In addition, for example, the statistical information is information in which the distribution of the analysis values is summarized in a time series, and may be expressed such that the characteristics of the time series can be grasped. As an example, the statistical information may be a time series graph (trend graph). It is needless to say that the information may be different from the time series graph.

For example, the time series graph may be a graph illustrating a regression line obtained by performing regression analysis of analysis data for each time series. For example, the time series graph may include the slope of the regression line, the presence or absence (p value) of a statistically significant difference, and the like.

<Display Control Unit>

The ophthalmologic information analysis apparatus of the present illustrative embodiment may include a display control unit (for example, CPU 13). The display control unit displays the first analysis data based on the first OCT data and the second analysis data based on the second OCT data on the display unit (for example, display unit 12) in a comparable manner. For example, the display control unit may display the first analysis data and the second analysis data side by side, or may display the first analysis data and the second analysis data in a switchable manner. In addition, for example, the display control unit may display the first analysis data and the second analysis data over time.

It is needless to say that, in a case where the third OCT data is obtained by the third acquisition unit, the display control unit may display at least two analysis data out of the first analysis data, the second analysis data, and the third analysis data. For example, at least one of the first analysis data and the second analysis data, and the third analysis data may be displayed. In addition, for example, the first analysis data, the second analysis data, and the third analysis data may all be displayed.

The display control unit may display the follow-up observation data acquired by the analysis unit on the display unit. For example, among the first analysis data, the second analysis data, and the third analysis data, the follow-up observation data corresponding to at least two analysis data may be displayed, or the follow-up observation data corresponding to all of the analysis data may be displayed. For example, the display of the follow-up observation data makes it easier to grasp the tendency of the analysis region with change over time, and the follow-up observation of the subject eye can be efficiently performed.

The display control unit may set analysis data in which the analysis regions in the subject eye at least partially overlap as a target, and displays the analysis data on the display unit in a comparable manner. For example, accordingly, the scanning range of the measurement light is different, but it is possible to easily compare analysis data including the same analysis region.

In the ophthalmologic information analysis apparatus of the present illustrative embodiment, the first OCT data including the analysis region, which is obtained by scanning the measurement light in the transverse direction in the first scanning range is acquired, and the second OCT data including at least the analysis region, which is obtained by scanning the measurement light in the transverse direction in the second scanning range being captured at a date and time different from that of the first OCT data may be acquired. Regardless of the difference between the first scanning range and the second scanning range, the analysis region common to the first OCT data and the second OCT data may be specified, and the analysis region common to the first OCT data and the second OCT data may be displayed on the display unit in a comparable manner. For example, accordingly, even in a case where the scanning range of the measurement light in the optical coherence tomography is widened and the OCT data with different scanning ranges is obtained for the same subject eye, the follow-up observation can be efficiently performed.

The present disclosure is not limited to the apparatus described in the present illustrative embodiment. For example, terminal control software (program) that performs the functions of the above-described illustrative embodiment is supplied to the system or apparatus via a network or various storage media, and the control device (for example, CPU or the like) of the system or apparatus can also read and execute the program.

Example

An example of an ophthalmologic information analysis apparatus 1 in the present illustrative embodiment will be described.

FIG. 1 is a configuration view of the ophthalmologic information analysis apparatus 1. The ophthalmologic information analysis apparatus 1 includes an input unit 11, a display unit 12, a central processing unit (CPU) 13, a storage unit 14, and the like. Each part is electrically connected to each other via a bus or the like.

The ophthalmologic information analysis apparatus 1 is connected to an optical coherence tomography (OCT) 2 in a state where signals can be transmitted and received. The ophthalmologic information analysis apparatus 1 may be connected to the plurality of optical coherence tomography including a first optical coherence tomography A (hereinafter, first device 21) and a second optical coherence tomography B (hereinafter, second device 22) as the optical coherence tomography 2. In the ophthalmologic information analysis apparatus 1, the first device 21 and the second device 22 are not necessarily connected to each other at the same time, and a case where the optical coherence tomography is changed from the first device 21 to the second device 22 can also be included in the long-term follow-up observation.

The input unit 11 is configured for the operator of the ophthalmologic information analysis apparatus 1 to input various types of information. For example, the input unit 11 may be a touch panel, a keyboard, a mouse, or the like. The display unit 12 displays on the screen the OCT data obtained by the optical coherence tomography 2, the analysis result of the OCT data, the follow-up observation data obtained from the analysis result of the OCT data, and the like. For example, the OCT data may be an OCT tomographic image. For example, the analysis result of the OCT data may be a retina thickness information, a retina thickness map image generated based on the retina thickness information, an analysis chart calculated based on the retina thickness information, or the like. For example, the follow-up observation data may be a time series graph (trend graph) or the like. The CPU 13 is a processor that performs overall arithmetic processing in the ophthalmologic information analysis apparatus 1. The CPU 13 has an image processing function for performing image processing of various images acquired by the ophthalmologic information analysis apparatus 1.

The storage unit 14 stores the ophthalmologic information analysis program. The storage unit 14 stores the OCT data, the analysis results of the OCT data, the follow-up observation data, and the like. For example, the analysis result and the follow-up observation data of the OCT data, which are obtained on different days by the optical coherence tomography 2, are stored. This includes the analysis results and the follow-up observation data for each examination date for each subject. Furthermore, the storage unit 14 stores imaging conditions (for example, examination date, scanning conditions, detection conditions, and the like) at the time of OCT data acquisition. For example, the scanning conditions may be a scanning pattern, a scanning range, a scanning density, a scanning position, a scanning site (for example, macula, optic papilla, and the like), and the like. For example, the detection condition may be the exposure time of the detector, or the like. For example, the storage unit 14 may be a hard disk drive, a flash ROM, a USB memory, or the like.

By using an input unit, a display unit, an arithmetic processing unit, and a storage unit of a commercially available personal computer (PC) as the input unit 11, the display unit 12, the CPU 13, and the storage unit 14 of the ophthalmologic information analysis apparatus 1, an ophthalmologic information analysis program may be installed on the commercially available PC. It is needless to say that, as the input unit 11, the display unit 12, the CPU 13, and the storage unit 14 of the ophthalmologic information analysis apparatus 1, the input unit, the display unit, the arithmetic processing unit, and the storage unit, which are included in the optical coherence tomography 2, may be used.

The ophthalmologic information analysis apparatus 1 in the present example is, for example, a computer, and the CPU 13 executes the program by reading the above-described ophthalmologic information analysis program on the RAM and then performing various arithmetic processing. For example, the CPU 13 controls the display screen of the display unit 12 according to the ophthalmologic information analysis program.

The optical coherence tomography 2 is a device that acquires OCT data of the fundus of the subject eye. The optical coherence tomography 2 may be a Fourier domain OCT (for example, spectrum domain OCT, wavelength sweep type OCT, and the like). The optical coherence tomography 2 may be a time domain OCT. The OCT data obtained by using the optical coherence tomography 2 may be analyzed by the control unit that controls the optical coherence tomography 2, or may be analyzed by another control unit. Accordingly, the analysis result (for example, retina thickness information) regarding the fundus of the subject eye is acquired.

The optical coherence tomography 2 includes an OCT optical system that detects a coherence signal due to the measurement light and reference light applied to the subject eye, and acquires the OCT data of the subject eye by processing the coherence signal. The OCT optical system may be configured to include a light source that emits low coherent light, an optical divider that divides the light emitted from the light source into measurement light and reference light, a measurement optical system that guides the measurement light to the subject eye, the scanning unit that scans the measurement light in the transverse direction on the fundus of the subject eye, a reference optical system that generates reference light, a detector that detects a coherence signal due to the synthesis of measurement light and reference light, and the like. It is needless to say that the OCT optical system may have a configuration different from these.

The optical coherence tomography 2 can obtain the OCT tomographic image as OCT data of the fundus of the subject eye based on the coherence signal due to the measurement light and the reference light. The optical coherence tomography 2 can obtain a three-dimensional OCT tomographic image (three-dimensional OCT data) as OCT data of the fundus of the subject eye based on the coherence signal due to the measurement light and the reference light. In addition, the optical coherence tomography 2 can obtain the OCT front image (OCT front data) from the three-dimensional OCT tomographic image as OCT data of the fundus of the subject eye. For example, in this case, an integrated image in which the spectral intensities of the coherence signals are integrated for each point in the XY directions may be obtained as the OCT front image.

The optical coherence tomography 2 may perform image processing on the three-dimensional OCT tomographic image to acquire the retina thickness information of the fundus. For example, as the retina thickness information, the thickness of each layer of the retina (specifically, the thickness of the optic nerve fiber layer, the thickness from the optic nerve fiber layer to the retinal pigment epithelial layer, and the like) is acquired. The optical coherence tomography 2 may acquire a two-dimensional retina thickness map image based on the retina thickness information. It is needless to say that the choroid information of the fundus may be acquired by performing image processing to the three-dimensional OCT tomographic image, or a two-dimensional choroid thickness map image may be acquired based on the choroid information.

Furthermore, the optical coherence tomography 2 may have a front observation optical system and may obtain a front image of the fundus of the subject eye. For example, a scanning type confocal camera optical system (SLO optical system) may be provided as the front observation optical system, and an SLO front image of the subject eye may be obtained. For example, the fundus camera optical system may be provided as the front observation optical system, and an infrared front image, a color front image, a fluorescence front image, or the like of the subject eye may be obtained.

In the present example, the first device 21 and the second device 22 scan the measurement light in the transverse direction in the scanning ranges different from each other on the subject eye. For example, in the first device 21, on the fundus of the subject eye, by scanning the measurement light in the transverse direction in the first scanning range, a first three-dimensional OCT tomographic image (hereinafter, first OCT tomographic image) obtained by imaging the fundus of the subject eye is obtained. In addition, for example, in the second device 22, on the fundus of the subject eye, by scanning the measurement light in the transverse direction in the second scanning range, a second three-dimensional OCT tomographic image (hereinafter, second OCT tomographic image) obtained by imaging the fundus of the subject eye is obtained.

At least a part of the first OCT tomographic image and the second OCT tomographic image may overlap in the XY directions. For example, both the first OCT tomographic image and the second OCT tomographic image may be an OCT tomographic image obtained by imaging the first analysis region of the fundus. In addition, for example, the first OCT tomographic image may be an OCT tomographic; image obtained by imaging the first analysis region of the fundus, and the second OCT tomographic image may be an OCT tomographic image obtained by imaging the first analysis region and the second analysis region of the fundus.

The analysis and display of OCT data using the ophthalmologic information analysis apparatus 1 will be described in detail.

Figure 2:
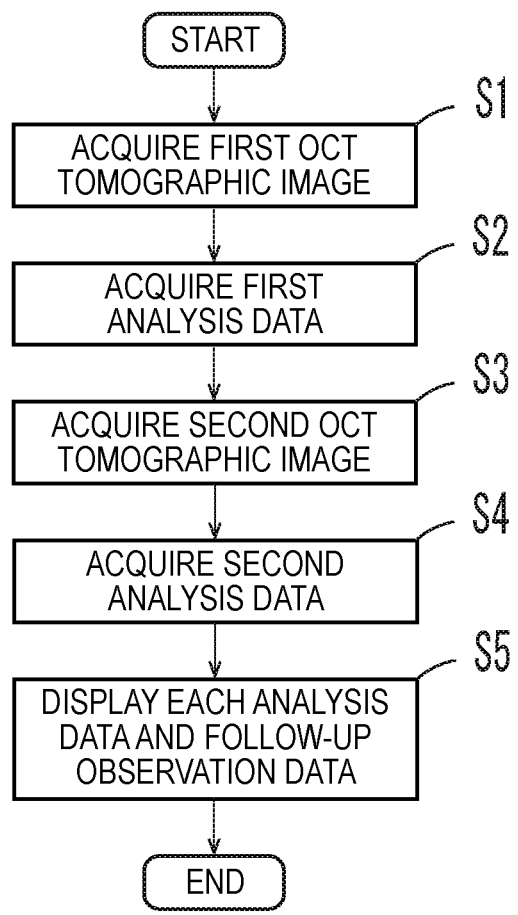
FIG. 2 is a flowchart illustrating an example of a control operation of a CPU.

FIG. 2 is a flowchart illustrating an example of a control operation of the CPU 13. In the present example, a case where, in the past, the first OCT tomographic image obtained by imaging the first analysis region of the fundus using the first device 21 is acquired, and on the following day, the second OCT tomographic image obtained by imaging the first analysis region and the second analysis region of the fundus using the second device 22, is described as an example. Here, the first analysis region of the fundus is exemplified as the macula, and the second analysis region of the fundus is exemplified as the optic papilla.

<Acquisition of OCT Tomographic Image (S1)>

At some point in the past, the examiner images the fundus of the subject eye with the first device 21. For example, the SLO front image (first SLO front image) of the subject eye is captured by the SLO optical system, and the first OCT tomographic image of the subject eye is captured by the OCT optical system. For example, the scanning conditions of the measurement light of the OCT optical system are set such that the macula is scanned at a predetermined scanning pattern (for example, raster scan), a predetermined scanning density (for example, 256 points in length×256 points in width), and a predetermined first scanning range (for example, a range of 6 mm in length×6 mm in width).

Accordingly, the first SLO front image and a first OCT tomographic image of the subject eye are obtained.

The control unit that controls the first device 21 associates the imaging conditions of the first SLO front image, the first OCT tomographic image, and the first OCT tomographic image with the subject information (for example, ID associated with each subject or the like), and transmits the associated imaging conditions to the CPU 13 of the ophthalmologic information analysis apparatus 1. The CPU 13 receives and stores these in the storage unit 14.

<Acquisition of First Analysis Data (S2)>

The CPU 13 analyzes the first OCT tomographic image and acquires the first analysis data Here, the macula map image created based on the first OCT tomographic image and the macula analysis chart calculated based on the first OCT tomographic image are acquired as the first analysis data. The CPU 13 may acquire at least one of the macula map image and the macula analysis chart as the first analysis data.

Figure 3A:
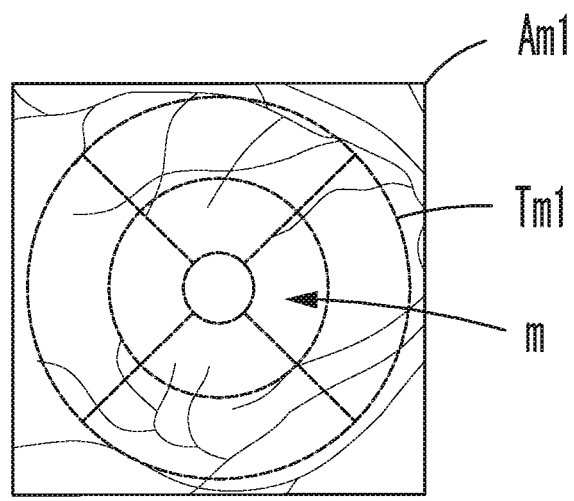
FIG. 3A and FIG. 3B are examples of first analysis data.
Figure 3B:
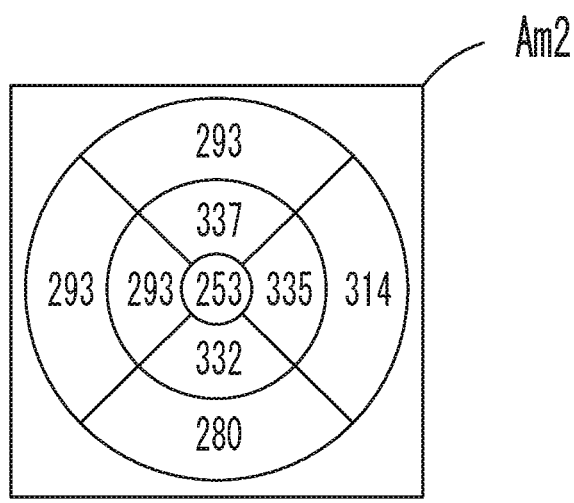

FIG. 3A and FIG. 3B are examples of the first analysis data FIG. 3A illustrates a macula map image Am1, and FIG. 3B illustrates a macula analysis chart Am2. For example, the macula map image Am1 is a color map image illustrating a two-dimensional distribution of the thickness of the retinal layer in the macula. The macula analysis chart Am2 is a chart obtained by averaging the two-dimensional distribution of the retina thickness in the macula for each region.

The CPU 13 calculates the thickness of each layer of the retina based on the first OCT data, and acquires the macula map image Am1 by two-dimensionally color-coding the thickness. The CPU 13 associates the positional relationship between the macula map image Am1 and the first SLO front image and stores the associated positional relationship in the storage unit 14.

The CPU 13 extracts a macula m from the macula map image Am1 and sets a target Tm1 indicating the region for obtaining the macula analysis chart Am2 in the macula m. The CPU 13 calculates the analysis value of the retina thickness for each section divided by the target Tm1. For example, the analysis value may be a value obtained by obtaining the fundamental statistics for each section. For example, the fundamental statistics may be a representative value (average value, median value, mode value, maximum value, minimum value, and the like), dispersal degree (variance, standard deviation, coefficient of variation, and the like) and the like. Accordingly, the CPU 13 acquires the macula analysis chart Am2 and stores the macula analysis chart Am2 in the storage unit 14.

At a certain time in the past when the fundus of the subject eye was captured by the first device 21, at least one of the macula map image Am1 and the macula analysis chart Am2 may be displayed on the screen of the display unit 12.

<Acquisition of Second OCT Tomographic Image (S3)>

The examiner images the fundus of the subject eye by the second device 22 after a lapse of time has passed since the fundus of the subject eye was captured by the first device 21. For example, the SILO front image (second SLO front image) of the subject eye is captured by the SLO optical system, and the second OCT tomographic image of the subject eye is captured by the OCT optical system. For example, second scanning conditions of the measurement light of the OCT optical system are set such that the macula and the optic papilla are scanned at a predetermined scanning pattern (for example, raster scan), a predetermined scanning density (for example, 256 points in length×256 points in width), and a predetermined second scanning range (for example, a range of 9 mm in length×12 mm in width).

Accordingly, the second SLO front image and the second OCT tomographic image of the subject eye are obtained.

The control unit that controls the second device 22 associates the imaging conditions of the second SLO front image, the second OCT tomographic image, and the second OCT tomographic image with the subject information, and transmits the associated imaging conditions to the CPU 13 of the ophthalmologic information analysis apparatus 1. The CPU 13 receives and stores these in the storage unit 14.

<Acquisition of Second Analysis Data (S4)>

The CPU 13 analyzes the second OCT tomographic image and acquires the second analysis data Here, the retina map image created based on the second OCT tomographic image and the macula analysis chart calculated based on the second OCT tomographic image are acquired as the second analysis data. The CPU 13 may acquire at least one of the retina map image and the macula analysis chart as the second analysis data.

Figure 4A:
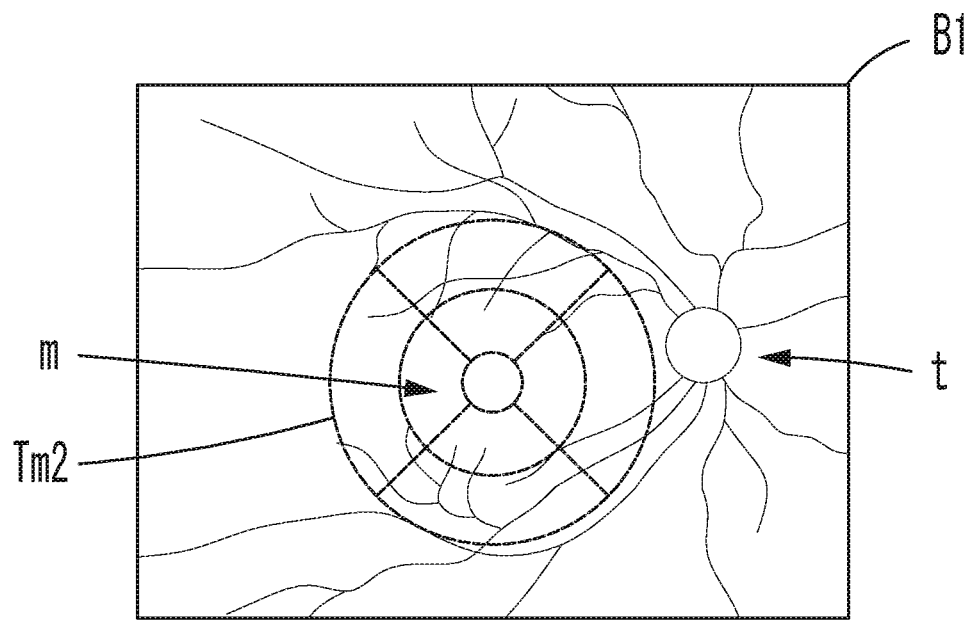
FIG. 4A and FIG. 4B are examples of second analysis data.
Figure 4B:
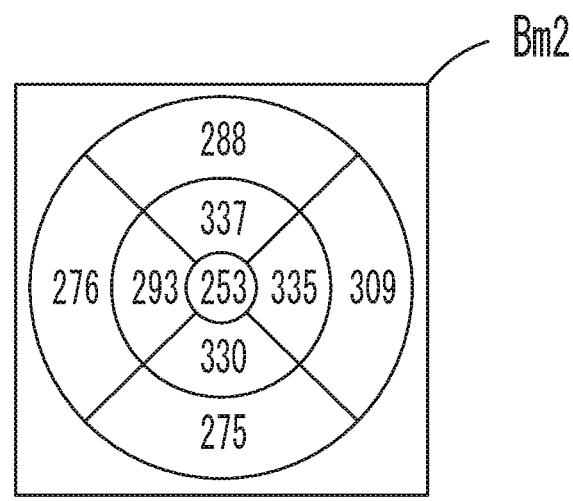

FIG. 4A and FIG. 4B are examples of the second analysis data FIG. 4A illustrates a retina map image B1, and FIG. 4B illustrates a macula analysis chart Bm2. For example, the retina map image B1 is a color map image illustrating a two-dimensional distribution of the thickness of the retinal layer in the macula and the optic papilla. The macula analysis chart Bm2 will be described later.

The CPU 13 calculates the thickness of each layer of the retina based on the second OCT data, and acquires the retina map image B1 by two-dimensionally color-coding the thickness. The CPU 13 associates the positional relationship between the retina map image B1 and the second SLO front image and stores the associated positional relationship in the storage unit 14.

In the present example, the CPU 13 sets the macula analysis chart Bm2 for the currently acquired retina map image B1 at the same site where the macula analysis chart Am2 is set for the macula map image Am1 acquired in the past. In other words, the CPU 13 sets the macula analysis chart Bm2 in the macula in the retina map image B1.

First, the CPU 13 aligns the macula map image Am1 with the retina map image B1. For this, the first SLO front image associated with the macula map image Am1 and the second SLO front image associated with the retina map image B1 may be used. For example, the CPU 13 extracts characteristic points (for example, macula, optic papilla, blood vessel, and the like) from the first SLO front image and the second SLO front image, and calculates the positional deviation direction and the positional deviation amount between the characteristic points in each SLO front image. In addition, for example, the CPU 13 automatically adjusts the relative positions of the first SLO front image and the second SLO front image based on the positional deviation direction and the positional deviation amount. The position adjustment between the first SLO front image and the second SLO front image may be executed semi-automatically, including manually. As the positional relationship between the first SLO front image and the second SLO front image changes, the positional relationship between the macula map image Am1 and the retina map image B1 also changes, and accordingly, the relative positions of the macula map image Am1 and the retina map image B1 are aligned.

Next, the CPU 13 detects an overlapping region Rm in which the macula map image Am1 and the retina map image B1 overlap each other. The CPU 13 obtains the luminance value for each pixel of the macula map image Am1 and the retina map image B1, and calculates the similarity between the two images based on the difference. For example, the CPU 13 compares the luminance values of the macula map image Am1 and the retina map image B1 for each pixel, and detects the division value or the subtraction value as the difference. The division value or the subtraction value may be binarized. Furthermore, for example, the CPU 13 calculates the average value of the differences as similarity. The CPU 13 shifts the position where the macula map image Am1 and the retina map image B1 are superimposed by one pixel (so-called template matching is performed), and calculates the similarity for all the combinations of pixels in the same manner.

The position where the macula map image A1 and the retina map image are superimposed and the similarity becomes zero indicates that the macula map image Am1 and the retina map image B1 are the same image. For example, the CPU 13 detects that the respective images overlap each other in a case where there is a combination of the macula map image Am1 and the retina map image B1 of which the similarity is less than a preset threshold value. At this time, for each combination of images having a similarity of zero (or a value closest to zero), the overlapping region Rm in which the macula map image Am1 and the retina map image B1 overlap each other is specified. In other words, the position of the macula in of the retina map image B1, corresponding to the position of the macula in of the macula map image Am1, is specified. For example, even in a case where a lesion appears in the map image due to the change over time, the CPU 13 obtains the difference in the luminance value corresponding to the site other than the lesion site and calculates the similarity, and accordingly, the same macula m (overlapping region Rm) can be specified by the macula map image Am1 and the retina map image B1. In addition, for example, in a case where the CPU 13 has only a combination of the macula map image Am1 and the retina map image B1 of which the similarity is equal to or higher than a preset threshold value, the CPU 13 may detect that the respective images do not overlap each other.

The calculation of the similarity is not limited to the method using the difference in the luminance values. For example, the calculation may also be performed based on the amount of change in the luminance value, the running of blood vessels, and the like.

The CPU 13 sets a target Tm2 indicating a region for obtaining the macula analysis chart Bm2 in the macula m corresponding to the macula map image Am1, that is, the macula m specified in the retina map image B1. The target Tm1 set for the macula map image Am1 and the target Tm2 set for the retina map image B1 are set to the same size. The CPU 13 calculates the analysis value for each section of the target Tm2. Accordingly, the CPU 13 acquires the macula analysis chart Bm2 and stores the macula analysis chart Bm2 in the storage unit 14.

<Display of Each Analysis Data and Follow-Up Observation Data (S5)>

Figure 5:
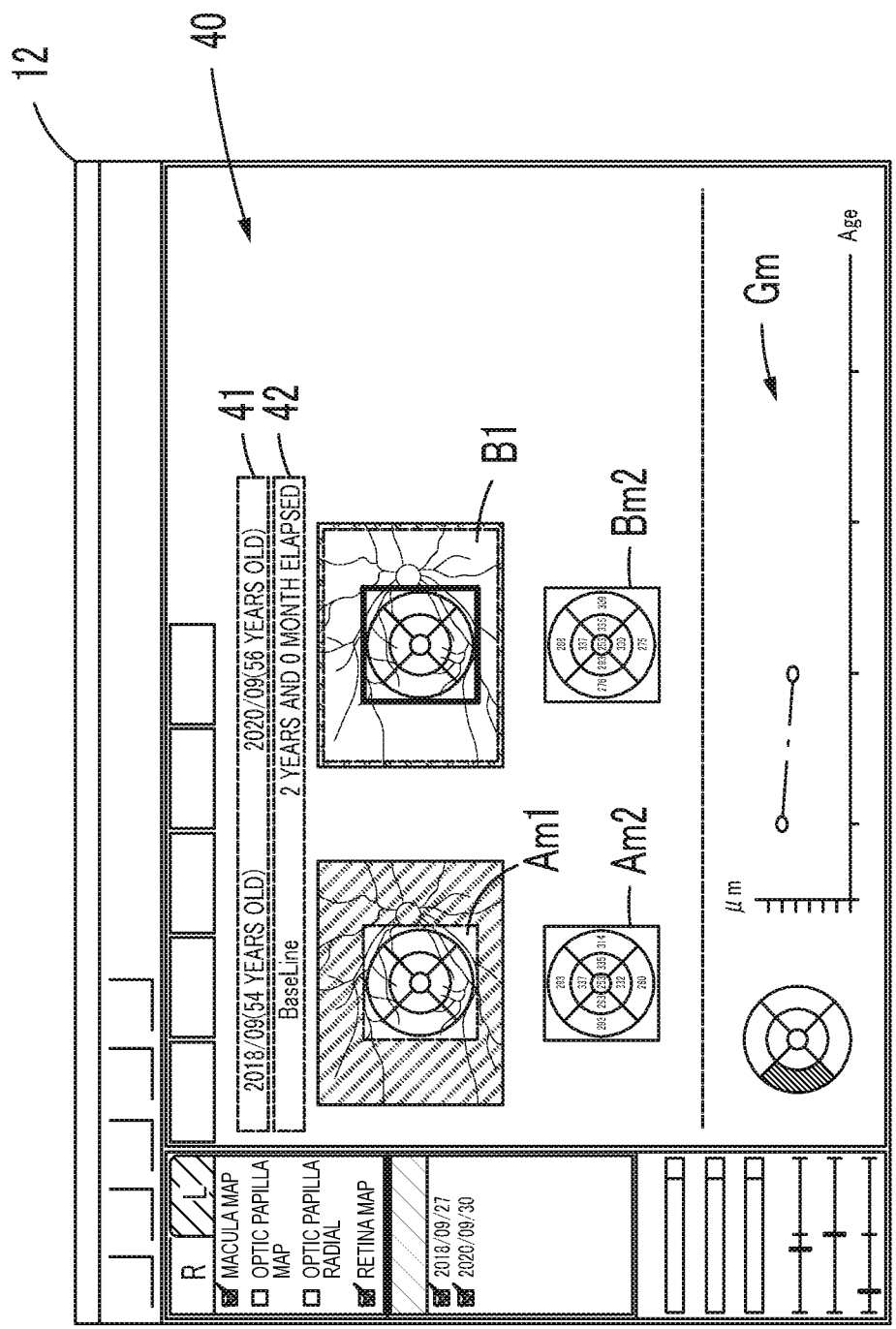
FIG. 5 is an example of a screen of a display unit.

FIG. 5 is an example of a screen of the display unit 12. On the display unit 12, a display screen 40 for displaying the first analysis data and the second analysis data in a comparable manner is formed. On the display screen 40, each result is arranged in a time series from left to right, and examination date information 41, baseline information 42, first analysis data (macula map image Am1 and macula analysis chart Am2), second analysis data (retina map image B1 and macula analysis chart Bm2), follow-up observation data (time series graph) described later, and the like are displayed.

For example, the examination date information 41 is information indicating the examination date and the age of the subject on the examination date. For example, the baseline information 42 is information indicating the temporal relationship of each analysis data. As an example, the oldest analysis data in each analysis data displayed on the display unit 12 is set as the baseline for follow-up observation. For other analysis data, the elapsed time (for example, year and month), of which the baseline is the start date, is calculated and displayed.

FIG. 6 is an example of the display screen 40 related to the macula m. The CPU 13 displays the first analysis data and the second analysis data side by side. For example, the CPU 13 displays the macula map image Am1 acquired in the past and the retina map image B1 acquired at present side by side. The macula map image Am1 may be superimposed on a corresponding first SLO front image F1, and the retina map image B1 may be superimposed on the corresponding second SLO front image F2. In the retina map image B1, a display that emphasizes the overlapping region Rm may be made such that the overlapping region Rm with the macula map image Am1 can be grasped. As an example, the overlapping region Rm may be surrounded by a frame. It is needless to say that a process of adjusting or hiding the luminance or contrast of a region different from the overlapping region Rm may be performed. For example, the CPU 13 displays the macula analysis chart Am2 acquired in the past and the macula analysis chart Bm2 acquired at present side by side.

In the first analysis data and the second analysis data, only each map image may be displayed, or only each analysis chart may be displayed. As described in the present example, in a case of displaying both each map image and each analysis chart, the set target position may be superimposed on each map image. In other words, the target Tm1 may be displayed to be superimposed on the macula map image Am1 and the target Tm2 may be displayed to be superimposed on the retina map image B1.

Furthermore, on the display screen 40, the follow-up observation data for the same region may be displayed based on the first analysis data and the second analysis data Here, as the follow-up observation data, a time series graph in which the retina thickness information for each examination date is arranged in a time series is displayed. The time series graph has a characteristic as a trend graph illustrating the tendency of the change over time of the retina thickness information for each examination date. The time series graph may be a line graph, a plot graph, or the like. The follow-up observation data may be data different from the time series graph, and may be, for example, data indicating difference information (for example, a difference map).

The CPU 13 displays a time series graph Gm in which the retina thickness of the macula m is plotted for each examination date. For example, in the time series graph Gm, the vertical axis is represented by the retina thickness and the horizontal axis is represented by time. The vertical axis may be a thickness value (for example, μm), a volume value (for example, mm$^3$), or the like as a numerical value indicating the retinal layer. The horizontal axis may be the age of the subject, the elapsed period from the start date of the follow-up observation, which is the baseline, and the like. It is needless to say that the relationship between the vertical axis and the horizontal axis may be reversed. The CPU 13 may analyze the tendency of the retina thickness on each examination date and display the time-series regression line T based on the retina thickness information on each examination date. The CPU 13 may calculate and display a slope Tg of the regression line T.

As described above, for example, the ophthalmologic information analysis apparatus in the present example specifies the analysis region corresponding to the first analysis data from the second OCT data regardless of the difference in the scanning range of the measurement light when the subject eye is captured by the optical coherence tomography, acquires the second analysis data obtained by analyzing the analysis region in the second OCT data, and displays the first analysis data and the second analysis data in a comparable manner. Accordingly, the analysis regions included in each OCT data can be associated (matched) with each other, and the analysis data in the same analysis region can be extracted and easily compared. For example, even when the scanning range that can be captured by the old apparatus and the new apparatus changes by replacing the optical coherence tomography with a new apparatus, the analysis data of each apparatus can be easily compared. Therefore, the follow-up observation of the subject eye is efficiently performed.

For example, the ophthalmologic information analysis apparatus in the present example acquires the follow-up observation data for observing the progress of the analysis region in the subject eye and displays the follow-up observation data. For example, by confirming the follow-up observation data based on each analysis data, it becomes easier to grasp the tendency of the analysis region with change over time, and the follow-up observation of the subject eye is efficiently performed.

Modified Example

In the present example, the configuration for acquiring the macula map image Am1 by using the first device 21 has been described as an example, but the present disclosure is not limited thereto. In the present example, a configuration for obtaining the first OCT tomographic image of an optic papilla t and acquiring an optic papilla map image At1 of the optic papilla t by using the first device 21, may be employed. In addition, in the present example, a configuration of obtaining the first OCT tomographic image of each of the macula m and the optic papilla t and acquiring the macula map image Am1 of the macula m and the optic papilla map image At1 and the optic papilla t by using the first device 21, may be employed.

First, a case where the optic papilla map image At1 is obtained using the first device 21 will be described. In the second device 22, the retina map image B1 is acquired in the same manner.

FIG. 7 is an example of the display screen 40 related to the optic papilla t. For example, the CPU 13 extracts the optic papilla t from the optic papilla map image At1 obtained in the past, sets a target Tt1 on the optic papilla t, and acquires an optic papilla analysis chart At2. In addition, for example, when the CPU 13 specifies the optic papilla t of the retina map image B1 by detecting the overlapping region Rt of the optic papilla map image At1 obtained in the past and the retina map image B1 obtained at present, the CPU 13 sets a target Tt2 on the optic papilla t, and acquires the optic papilla analysis chart Bt2. The CPU 13 displays the optic papilla map image At1 and the retina map image B1 side by side. In addition, the CPU 13 displays the optic papilla analysis chart At2 and the optic papilla analysis chart Bt2 side by side. It is needless to say that the CPU 13 may display a time series graph Gt in which the retina thickness of the optic papilla t is plotted for each examination date.

Next, a case where the macula map image Am1 and the optic papilla map image At1 are obtained by using the first device 21 will be described. In the second device 22, the retina map image B1 is acquired in the same manner.

Figure 8:
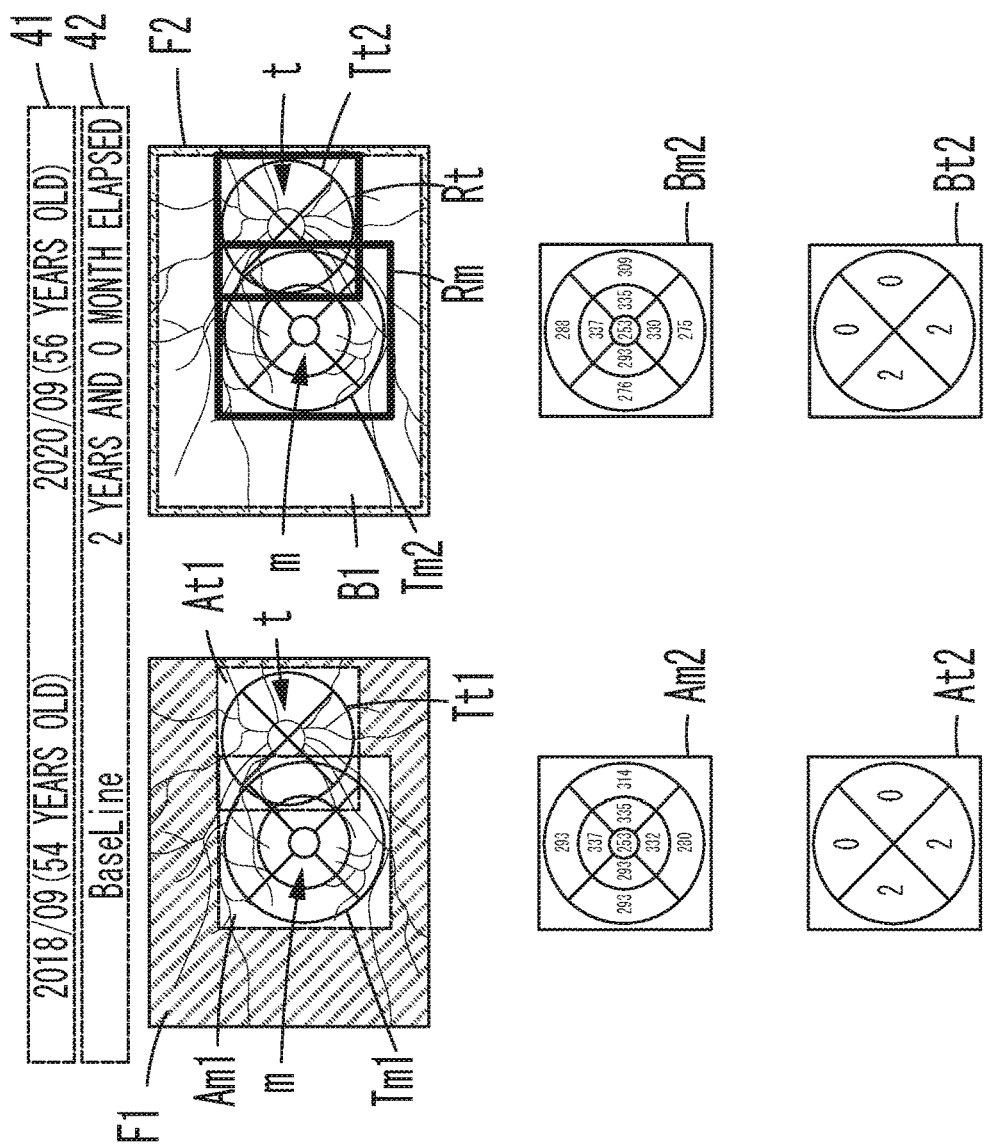
FIG. 8 is an example of the display screen related to the macula and the optic papilla.

FIG. 8 is an example of the display screen 40 related to the macula m and the optic papilla t. For example, the CPU 13 can acquire the analysis data for the macula m (macula analysis chart Am2 and macula analysis chart Bm2) and the analysis data for the optic papilla t (optic papilla analysis chart At2 and optic papilla analysis chart Bt2), as described above. The CPU 13 displays the macula map image Am1 and the optic papilla map image At1 which are obtained in the past, and the retina map image B1 obtained at present side by side. For example, both the macula map image Am1 and the optic papilla map image At1 may be displayed at the same time by being superimposed on the first SLO front image F1. For example, in the retina map image B1, the overlapping region Rm of the macula m and the overlapping region Rt of the optic papilla t may be displayed at the same time. The CPU 13 displays the macula analysis chart Am2 and the macula analysis chart Bing side by side, and displays the optic papilla analysis chart At2 and the optic papilla analysis chart Bt2 side by side.

The CPU 13 may acquire follow-up observation data for observing the progress of the analysis region of the subject eye and display the acquired follow-up observation data on the display unit 12. Here, based on the first OCT tomographic images of each of the macula m and the optic papilla t, the first analysis data for each of the macula m and the optic papilla t is obtained. In addition, based on the second OCT tomographic images including both the macula m and the optic papilla t, the second analysis data for each of the macula m and the optic papilla t is obtained. Therefore, the CPU 13 may display the follow-up observation data for the same region based on the first analysis data and the second analysis data. In other words, the time series graph Gm for the macula m and the time series graph Gt for the optic papilla t may be displayed. For example, accordingly, it becomes easier to grasp the tendency of the analysis region with change over time, and the follow-up observation of the subject eye is efficiently performed.

In a case where the CPU 13 obtains each first OCT tomographic image for a plurality of analysis regions, the CPU 13 may analyze any of the plurality of analysis regions and display the analysis data. In addition, in a case where the CPU 13 obtains each first OCT tomographic image for a plurality of analysis regions, the CPU 13 may selectively analyze either the first analysis region or the second analysis region based on the set analysis region. Here, by obtaining the first OCT tomographic image of each of the macula m or the optic papilla t, either the macula m or the optic papilla t may be selectively analyzed.

For example, the input unit 11 or the display screen 40 may be provided with a setting button for setting a target analysis region. For example, as the examiner operates the setting button, the setting of the acquisition of the analysis data for the macula m and the acquisition of the analysis data for the optic papilla t may be switched. The CPU 13 analyzes the analysis region desired by the examiner based on the operation signal input by the examiner, and displays the analysis data on the display unit 12. For example, accordingly, it becomes possible to easily confirm the change over time in the desired analysis region.

For example, the ophthalmologic information analysis apparatus may acquire the first analysis data in which the first analysis region (macula) and the second analysis region (optic papilla) are individually analyzed based on the plurality of first OCT data. At least one of the first analysis region and the second analysis region corresponding to the first analysis data may be specified, and the second analysis data obtained by analyzing at least one of the first analysis region and the second analysis region in the second OCT data may be acquired. Accordingly, for example, even in a case where there are the plurality of OCT data having different scanning ranges of the measurement light, the analysis data in each analysis region can be easily compared.

In the present example, the configuration for acquiring the retina map image B1 captured in the second scanning range by using the second device 22 has been described as an example, but the present disclosure is not limited thereto. In the present example, the retina map image C1 captured in the same second scanning range may be acquired by using the second device 22 after a further lapse of time has passed since the second device 22 was used.

Figure 9:
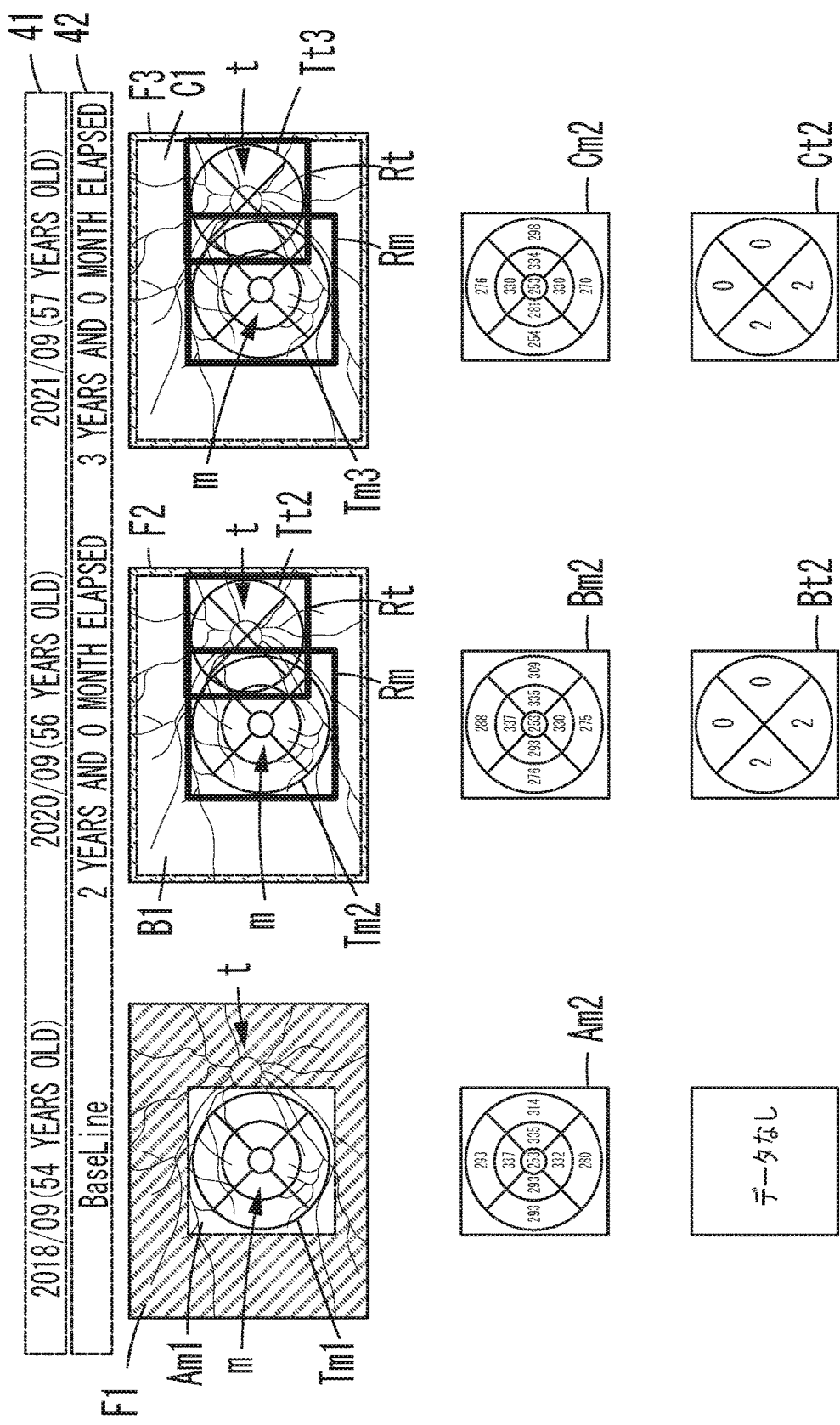
FIG. 9 is an example of the display screen in a case where a retina map image is obtained.

FIG. 9 is an example of the display screen 40 in a case where the retina map image C1 is obtained. The CPU 13 aligns the macula map image Am1 acquired by using the first device 21 and set as the baseline with the retina map image C1 currently acquired by using the second device 22. For example, the first SLO front image F1 associated with the macula map image Am1 and a third SLO front image F3 associated with the retina map image C1 are used. The CPU 13 detects the overlapping region Rm in which the macula map image Am1 and the retina map image C1 overlap each other, and specifies the macula m of the retina map image C1 corresponding to the macula m of the macula map image Am1. In addition, the CPU 13 sets a target Tm3 having the same size as the target Tm1 set in the macula map image Am1 in the retina map image C1. Accordingly, a macula analysis chart Bm3 is acquired.

Here, since the macula map image Am1 set as the baseline and the retina map image B1 acquired by using the second device 22 are aligned at a time in the past, the CPU 13 can align the retina map image B1 and the retina map image C1. In this case, the macula m of the retina map image C1 corresponding to the macula m of the retina map image B1 is specified, and the optic papilla t of the retina map image B1 and the corresponding optic papilla t of the retina map image C1 are specified. The CPU 13 may set a target Tt3 having the same size as the target Tt2, which is set in the retina map image B1, in the retina map image C1, and accordingly, an optic papilla analysis chart Bt3 may be acquired. In other words, for the optic papilla t, the optic papilla analysis chart Bt3 may be acquired by setting the retina map image B1 as the baseline.

The CPU 13 displays each map image obtained in this manner and each analysis chart side by side. It is needless to say that, although not illustrated in FIG. 9, as the follow-up observation data, the time series graph Gm of the macula m and the time series graph GE of the optic papilla t may be displayed. Since the macula map image Am1 does not include the optic papilla t, a notification in which there is no data corresponding to the optic papilla analysis chart At2 may be displayed.

In the above, a case where both the macula m and the optic papilla t are analyzed has been exemplified, but these may be selectable. At this time, the CPU 13 sets the oldest analysis data including the selected part as a baseline for follow-up observation, and displays each result side by side in a time series. For example, in a case where the macula m is selected, only the results for the macula m may be obtained. The CPU 13 may display the retina map image B1 and the macula analysis chart Bm2, and the retina map image C1 and the macula analysis chart Cm2, using the macula map image Am1 and the macula analysis chart Am1 as baselines. For example, in a case where the optic papilla t is selected, only the result for the optic papilla t may be obtained. The CPU 13 may display the retina map image C1 and the optic papilla analysis chart Ct2 with the retina map image B1 and the optic papilla analysis chart Bt2 as baselines.

For example, in this manner, the ophthalmologic information analysis apparatus may acquire the third OCT data captured in the same scanning range as that of the second OCT data on a day different from the day when the first OCT data and the second OCT data are captured. The third analysis data obtained by specifying and analyzing the analysis region corresponding to the first analysis data or the second analysis data may be acquired from the third OCT data. For example, in at least one of the first analysis data and the second analysis data, and the third analysis data, by displaying the same analysis region (that is, first analysis region, second analysis region, and the like) in a comparable manner, it becomes possible to easily confirm the change over time in the analysis region.

In the present example, the configuration in which all the map images are arranged in a time series with reference to the map image set as the baseline has been described as an example, but the present disclosure is not limited thereto. In the present example, each map image may be selectively arranged in a time series. In this case, the display unit 12 may display a setting screen for selecting desired analysis data.

FIG. 10 is an example of the setting screen 50. Each analysis data is displayed in a list on the setting screen 50. For example, examination date information 51, scanning condition information (for example, scanning site information 52, retina map image information 53, scanning range information 54, scanning density information 55, and the like), and the like are displayed on the setting screen.

The examination date information 51 is information indicating the examination date. The examination date information 51 may include the age of the subject on the examination date, in addition to the examination date. The scanning site information 52 is a site (for example, macula, optic papilla, and the like) where the measurement light was scanned at the time of imaging the subject eye. The retina map image information 53 is information indicating whether or not the retina map image has been obtained. The scanning range information 54 is the size of the scanning range (for example, 6 mm in length×6 mm in width, and the like) obtained by scanning the measurement light at the time of imaging the subject eye. The scanning density information 55 is the density (for example, 256 points in the length×256 points in the width, and the like) obtained by scanning the measurement light at the time of imaging the subject eye. For example, by displaying these information, it is possible to easily confirm whether each analysis data is obtained under the same scanning condition or under different scanning conditions.

A selection box 56 is displayed on the setting screen 50. The selection box 56 is a box for selecting the analysis data to be displayed on the display screen 40. For example, the examiner selects the desired analysis data (for example, a click operation on the selection box 56). The CPU 13 displays the corresponding analysis data on the display unit 12 based on the operation signal generated by the selection of the selection box 56. For example, in this manner, by making it possible to select the analysis data for each examination date, it is possible to appropriately perform the follow-up observation of the subject eye. As an example, data having low image quality on a certain examination date can be excluded and displayed. In addition, as an example, it is possible to display only the data in which the analysis data for the macula m (or the optic papilla t) exists.

Each analysis data is not limited to the list format, and may be displayed in various formats. For example, the data may be displayed in a tree format. In this case, the scanning site information 52, the scanning range information 54, the scanning density information 55, and the like may be indicated as tree items. Each analysis data may be displayed in a state where the data having overlapping regions are selected in advance (that is, in a state where the corresponding selection box 56 is selected in advance).

In the present example, the configuration in which template matching is used for detecting the overlapping region Rm between the macula map image Am1 and the retina map image B1 based on the OCT data has been described as an example, but the present disclosure is not limited thereto. In the present example, the overlapping region Rm may be detected based on the scanning conditions associated with the OCT data. As an example, in this case, the CPU 13 may store the scanning position or the scanning range in which scanning with the measurement light is performed in the storage unit 14 in association with each OCT data. The CPU 13 may compare the scanning position or the scanning range of the measurement light between the respective OCT data, and determine whether or not the overlapping region Rm exists based on the comparison result.

In the present example, the configuration in which the control unit of the first device 21 transmits the first OCT tomographic image to the CPU 13 of the ophthalmologic information analysis apparatus 1 has been described as an example, but the present disclosure is not limited thereto. For example, the control unit of the first device 21 may acquire the macula map image A1 or a first analysis chart A2 based on the first OCT tomographic image and transmit the acquired result to the CPU 13.

In the present example, the configuration in which the macula map image A1 and the retina map image B1 are aligned by using the first SLO front image and the second. SLO front image has been described as an example, but the present disclosure is not limited thereto. For example, by using the first OCT tomographic image and the second OCT tomographic image, the positions of the macula map image A1 and the retina map image B1 are aligned. In this case, the first OCT tomographic image and the second OCT tomographic image are integrated with each other to acquire each of the OCT front images, and based on these images, by performing the extraction of the characteristic points and the adjustment of the position based on the positional deviation direction and the positional deviation amount between the characteristic points in the same manner, the positions of the macula map image A1 and the retina map image B1 can be aligned.

However, in a case where at least one of the first OCT tomographic image and the second OCT tomographic image is obtained by scanning a small region (for example, a region of 3 mm in length×3 mm in width, and the like), it is difficult to extract the characteristic points from each of the OCT front images, and it is difficult to adjust the position using the characteristic points. Therefore, the CPU 13 may exclude the corresponding image from the target of alignment, or may display on the display unit 12 that the corresponding image is not suitable for alignment. The CPU 13 may switch the alignment using each of the OCT front images to the alignment using each of the SLO front images.

In the present example, the configuration in which at least a part of the first OCT tomographic image and the second OCT tomographic image overlap in the XY direction has been described as an example, but the present disclosure is not limited thereto. For example, these tomographic images may be configured such that at least a part thereof overlaps in the Z direction. For example, the first OCT tomographic image may be a tomographic image obtained by imaging the retina, and the second OCT tomographic image may be a tomographic image obtained by imaging the part from the retina to the choroid. Even in such a case, the ophthalmologic information analysis apparatus 1 may obtain the analysis data obtained by analyzing each of the OCT tomographic images in the same manner and display the obtained analysis data in a comparable manner.

At this time, in the first OCT tomographic image and the second OCT tomographic image, the display positions in the Z direction (depth direction) may be aligned. For example, the CPU 13 may detect each layer of the retina and align the display positions such that a predetermined layer is disposed at the center of the tomographic image. At this time, in the first OCT tomographic image and the second. OCT tomographic image, the slope of the retinal layer caused by the fact that the face of the subject is inclined with respect to the OCT optical system may be aligned. For example, the CPU 13 may align the slope of the retinal layer by calculating the slope of a predetermined layer of the retina and rotating at least one of each of the tomographic images based on the calculation. At this time, in the first OCT tomographic image and the second OCT tomographic image, the display sizes of the overlapping region may be aligned. For example, by specifying the overlapping regions between each of the tomographic images and enlarging or reducing at least one of each of the tomographic images, the CPU 13 may align the display size.

In the first device 21 and the second device 22, in the OCT optical system, the OCT tomographic images in which the scanning ranges of the measurement light and the scanning patterns of the measurement light are different may be acquired. For example, a line scan is set in the first device 21, a multi-scan (for example, five lines in each of the vertical direction and the horizontal direction, and the like) is set in the second device 22, and accordingly, each OCT tomographic image can be acquired. For example, in this case, the CPU 13 may specify the line closest to the scan line that configures the line scan in the second OCT tomographic image among the scan lines that configure the multi-scan in the second OCT tomographic image, and display the analysis data on the display unit 12.

In the first device 21 and the second device 22, there is a case where deviation or distortion occurs in the first OCT tomographic image and the second OCT tomographic image (third OCT tomographic image) due to the difference in the optical members that configure the OCT optical system. Therefore, the CPU 13 may acquire the analysis data in a state where the deviation or distortion between each of the tomographic images is corrected. For example, in this case, the CPU 13 may acquire information on the deviation or distortion of the first device 21 and the second device 22 in advance, and correct the tomographic image based on the information. In addition, for example, in this case, the CPU 13 may correct the tomographic image based on the scanning conditions of the measurement light.

Furthermore, in the first device 21 and the second device 22, there is a case where the first OCT tomographic image and the second OCT tomographic image (third OCT tomographic image) have different pixel densities due to differences in the wavelength of the measurement light in the OCT optical system, the resolution of the detector, and the like. Therefore, the CPU 13 may acquire the analysis data in a state where each of the tomographic images are corrected considering the resolution.

What is claimed is:

1. An ophthalmologic information analysis apparatus for analyzing OCT data captured by scanning a subject eye with measurement light by an optical coherence tomography, the apparatus comprising:
    a display; and
    a central processing unit configured to:
        acquire first analysis data obtained by analyzing an analysis region of the subject eye in first OCT data including the analysis region, the analysis region being obtained by scanning the measurement light in a transverse direction in a first scanning range on the subject eye;
        acquire second OCT data captured on a day different from that of the first OCT data, the second OCT data including at least the analysis region obtained by scanning the measurement light in the transverse direction in a second scanning range different from the first scanning range on the subject eye;
        perform an analysis comprising:
            specifying the analysis region corresponding to the first analysis data from the second OCT data; and
            acquiring second analysis data obtained by analyzing the analysis region in the second OCT data, regardless of a difference between the first scanning range and the second scanning range; and
        control the display to display the first analysis data and the second analysis data in a comparable manner,
    wherein the first OCT data is a plurality of pieces of data including data including a first analysis region as the analysis region and data including a second analysis region different from the first analysis region as the analysis region, in which the first scanning ranges are different from each other,
    wherein the central processing unit is configured to:
        acquire the first analysis data obtained by analyzing the first analysis region and the second analysis region in the acquiring of the first analysis data;
        acquire the second OCT data including both the first analysis region and the second analysis region as the analysis region in the acquiring of the second OCT data; and
        specify at least one of the first analysis region and the second analysis region corresponding to the first analysis data from the second OCT data, and acquire the second analysis data obtained by analyzing at least one of the first analysis region and the second analysis region in the second OCT data in the performing of the analysis.

2. The ophthalmologic information analysis apparatus according to claim 1, the central processing unit further configured to set the analysis region analyzed in the performing of the analysis,
    wherein in the performing of the analysis, the central processing unit is configured to selectively analyze any of the first analysis region or the second analysis region based on the analysis region set in the setting.

3. The ophthalmologic information analysis apparatus according to claim 1,
    wherein in the performing of the analysis, the central processing unit is configured to acquire follow-up observation data for observing a progress of the analysis region in the subject eye, and
    wherein in the controlling of the display, the central processing unit is configured to display the follow-up observation data on the display.

4. The ophthalmologic information analysis apparatus according to claim 1,
wherein in the controlling of the display, the central processing unit is configured to set analysis data in which the analysis regions in the subject eye at least partially overlap as a target, and display the analysis data on the display in a comparable manner.

5. The ophthalmologic information analysis apparatus according to claim 1, wherein the first analysis region is macula, and the second analysis region is optic papilla.

6. An ophthalmologic information analysis apparatus for analyzing OCT data captured by scanning a subject eye with measurement light by an optical coherence tomography, the apparatus comprising:
a display; and
a central processing unit configured to:
acquire first analysis data obtained by analyzing an analysis region of the subject eye in first OCT data including the analysis region, the analysis region being obtained by scanning the measurement light in a transverse direction in a first scanning range on the subject eye;
acquire second OCT data captured on a day different from that of the first OCT data, the second OCT data including at least the analysis region obtained by scanning the measurement light in the transverse direction in a second scanning range different from the first scanning range on the subject eye;
perform an analysis comprising:
specifying the analysis region corresponding to the first analysis data from the second OCT data; and
acquiring second analysis data obtained by analyzing the analysis region in the second OCT data, regardless of a difference between the first scanning range and the second scanning range; and
control the display to display the first analysis data and the second analysis data in a comparable manner,
acquire third OCT data including the analysis region, which is obtained by scanning the measurement light in the second scanning range on the subject eye being captured on a day different from that of the first OCT data and the second OCT data,
wherein in the performing of the analysis, the central processing unit is configured to specify the analysis region corresponding to the first analysis data or the second analysis data from the third OCT data, and acquires third analysis data obtained by analyzing the analysis region in the third OCT data, and
wherein in the controlling of the display, the central processing unit is configured to display at least one of the first analysis data and the second analysis data, and the third analysis data on the display unit in a comparable manner.

7. The ophthalmologic information analysis apparatus according to claim 6,
wherein in the performing of the analysis, the central processing unit is configured to specify the first analysis region corresponding to the first analysis data or the second analysis data from the third OCT data, and acquires the third analysis data obtained by analyzing the first analysis region in the third OCT data.

8. The ophthalmologic information analysis apparatus according to claim 6,
wherein in the performing of the analysis, the central processing unit is configured to specify the second analysis region corresponding to the first analysis data or the second analysis data from the third OCT data, and acquire the third analysis data obtained by analyzing the second analysis region in the third OCT data.

9. The ophthalmologic information analysis apparatus according to claim 6, wherein in the performing of the analysis, the central processing unit is configured to acquire follow-up observation data for observing a progress of the analysis region in the subject eye, and
wherein in the controlling of the display, the central processing unit is configured to display the follow-up observation data on the display.

10. The ophthalmologic information analysis apparatus according to claim 6, wherein in the controlling of the display, the central processing unit is configured to set analysis data in which the analysis regions in the subject eye at least partially overlap as a target, and display the analysis data on the display in a comparable manner.

11. A non-transitory computer-readable storage medium storing a program executed by a processor of an ophthalmologic information analysis apparatus for analyzing OCT data captured by scanning a subject eye with measurement light by an optical coherence tomography, the program, when executed by the processor, causing the ophthalmologic information analysis apparatus to perform:
acquiring first analysis data obtained by analyzing an analysis region of the subject eye in first OCT data including the analysis region, which is obtained by scanning the measurement light in a transverse direction in a first scanning range on the subject eye;
acquiring second OCT data including at least the analysis region, which is obtained by scanning the measurement light in the transverse direction in a second scanning range different from the first scanning range on the subject eye being captured on a day different from that of the first OCT data;
an analysis comprising:
specifying the analysis region corresponding to the first analysis data from the second OCT data; and
acquiring second analysis data obtained by analyzing the analysis region in the second OCT data, regardless of a difference between the first scanning range and the second scanning range; and
controlling a display to display the first analysis data and the second analysis data in a comparable manner,
wherein the first OCT data is a plurality of pieces of data including data including a first analysis region as the analysis region and data including a second analysis region different from the first analysis region as the analysis region, in which the first scanning ranges are different from each other,
wherein the central processing unit is configured to:
acquire the first analysis data obtained by analyzing the first analysis region and the second analysis region in the acquiring of the first analysis data;
acquire the second OCT data including both the first analysis region and the second analysis region as the analysis region in the acquiring of the second OCT data; and
specify at least one of the first analysis region and the second analysis region corresponding to the first analysis data from the second OCT data, and acquire the second analysis data obtained by analyzing at least one of the first analysis region and the second analysis region in the second OCT data in the performing of the analysis.

* * * * *